(12) United States Patent
Tao et al.

(10) Patent No.: US 10,408,757 B2
(45) Date of Patent: Sep. 10, 2019

(54) PLASMONIC IMAGING AND DETECTION OF SINGLE DNA MOLECULES

(71) Applicant: Arizona Board of Regents on Behalf of Arizona State University, Scottsdale, AZ (US)

(72) Inventors: Nongjian Tao, Scottsdale, AZ (US); Hui Yu, Scottsdale, AZ (US); Xiaonan Shan, Scottsdale, AZ (US); Shaopeng Wang, Scottsdale, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 357 days.

(21) Appl. No.: 15/038,629

(22) PCT Filed: Jan. 2, 2015

(86) PCT No.: PCT/US2015/010018
§ 371 (c)(1),
(2) Date: May 23, 2016

(87) PCT Pub. No.: WO2015/103459
PCT Pub. Date: Jul. 9, 2015

(65) Prior Publication Data
US 2016/0299069 A1    Oct. 13, 2016

Related U.S. Application Data

(60) Provisional application No. 61/923,477, filed on Jan. 3, 2014.

(51) Int. Cl.
*G01N 21/552* (2014.01)
*C12M 1/34* (2006.01)

(52) U.S. Cl.
CPC .......... *G01N 21/553* (2013.01); *C12M 41/46* (2013.01); *G01N 21/552* (2013.01)

(58) Field of Classification Search
CPC ........................... C12M 4/146; G01N 21/553
See application file for complete search history.

(56) References Cited

U.S. PATENT DOCUMENTS

| | | |
|---|---|---|
| 7,345,754 B1 | 3/2008 | Zhao et al. |
| 2008/0129981 A1 | 6/2008 | Nolte et al. |

(Continued)

OTHER PUBLICATIONS

Efcavitch JW, Thompson JF. (2010) Single-molecule DNA analysis. Annu Rev Anal Chem 3:109-28.

(Continued)

*Primary Examiner* — Hina F Ayub
*Assistant Examiner* — Amanda Merlino
(74) *Attorney, Agent, or Firm* — Yakov S. Sidorin; Quarles & Brady LLP

(57) ABSTRACT

Method and system to remove background noise with a differential approach in optical imaging is disclosed. The differential approach moves the sample position laterally over a small distance, and a differential image is generated from the images recorded before and after the lateral translation. This approach can significantly improve the image quality of objects, including single DNA molecules, for label-free optical imaging techniques, such as surface plasmon resonance imaging. Disclosed imaging technique provides high-resolution genome-wide restriction maps of single DNA molecules.

16 Claims, 11 Drawing Sheets

(56) References Cited

U.S. PATENT DOCUMENTS

2008/0231834 A1    9/2008    Gryczynski et al.
2012/0262565 A1    10/2012    Kahlman et al.

OTHER PUBLICATIONS

Lebofsky R, Bensimon A. (2002) Single DNA molecule analysis: Applications of molecular combing. Brief Funct Genomic Proteomic 1(4):385-96.
Wang WM, et al. (1997) Stretching DNA with optical tweezers. Biophysical Journal 72(3):1335-1346.
Teague B, et al. (2010) High-resolution human genome structure by single-molecule analysis. Proc Natl Acad Sci USA 107(24): 10848-10853.
Jing J, et al. (1998) Automated high resolution optical mapping using arrayed, fluid-fixed DNA molecules. Proc Natl Acad Sci USA 95(14): 8046-8051.
Chan TF, et al. (2006) A simple DNA stretching method for fluorescence imaging of single DNA molecules. Nucleic Acids Research 34(17): e113.
Gunther K, et al. (2010) Mechanical and structural properties of YOYO-1 complexed DNA. Nucleic Acids Research 38 (19):6526-6532.
Reuter M, Dryden DTF, (2010) The kinetics of YOYO-1 intercalation into single molecules of double-stranded DNA. Biochemical and Biophysical Research Communications 403(2): 225-229.
Thundat T, et al, (1994) Stretched DNA structure observed with atomic force microscopy. Nucleic Acids Research 22 (20):4224-4228.
Hansma HG, et al. (1995) Application for atomic force microscopy of DNA. Biophysical Journal 68(5):1672-1677.
Pastre D, et al. (2010) Specific DNA-protein interactions on mica investigated by atomic force microscopy. Langmuir 26(4): 2618-23.
Campbell CT, Kim G (2007) SPR microscopy and its applications to high-throughput analyses of biomolecular binding events and their kinetics. Biomaterials 28(15): 2380-2392.
Yao JM, et al. (2008) Seeing molecules by eye: Surface plasmon resonance imaging at visible wavelengths with high spatial resolution and submonolayer sensitivity. Angew Chem Int Edit 47:5013-5017.
Homola J (2008) Surface plasmon resonance sensors for detection of chemical and biological species. Chem Rev 108:462-493.
Wang S, et al. (2010) Label-free imaging, detection, and mass measurement of single viruses by surface plasmon resonance. Proc Natl Acad Sci USA 107(37): 16028-16032.
Shan X, et al. (2012) Imaging the electrocatalytic activity of single nanoparticles. Nature Nanotechnology 7:668-672.
Zimmermann RM, Cox EC (1994) DNA stretching on functionalized gold surfaces. Nucleic Acids Research 22(3): 492-497.
Bensimon A, et al. (1994) Alignment and sensitive detection of DNA by a moving interface. Science 265 (5181):2096-2098.
Hu J, et al. (1996) Imaging of single extended DNA molecules on flat (aminopropyl)triethoxysilane-mica by atomic force microscopy. Langmuir 12(7): 1697-1700.
Ma Y, et al. (2004) Polyaniline nanowires on Si surface fabricated with DNA templates. J. Am. Chem. Soc. 126(22): 7097-7101.
Huang B, Yu F, Zare RN (2007) Surface plasmon resonance imaging using a high numerical aperture microscope objective. Anal Chem 79(7):2979-2983.
Yu et al., "Plasmonic imaging and detection of single DNA molecules" ACS NANO 2014 8(4): 3427-3433.
International Search Report and the Written Opinion of the International Searching Authority in PCT/US15/10018, dated Apr. 1, 2015, pp. 1-11.

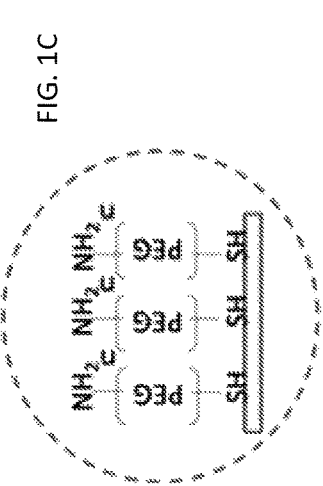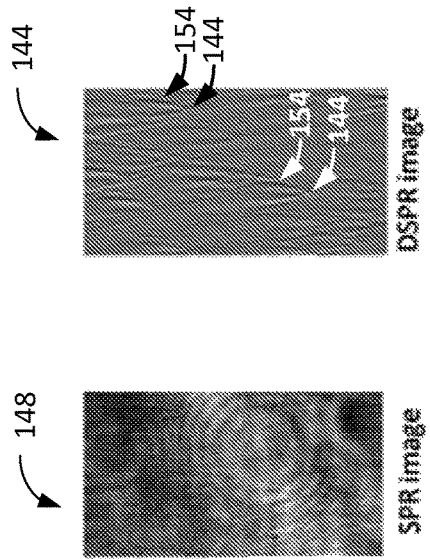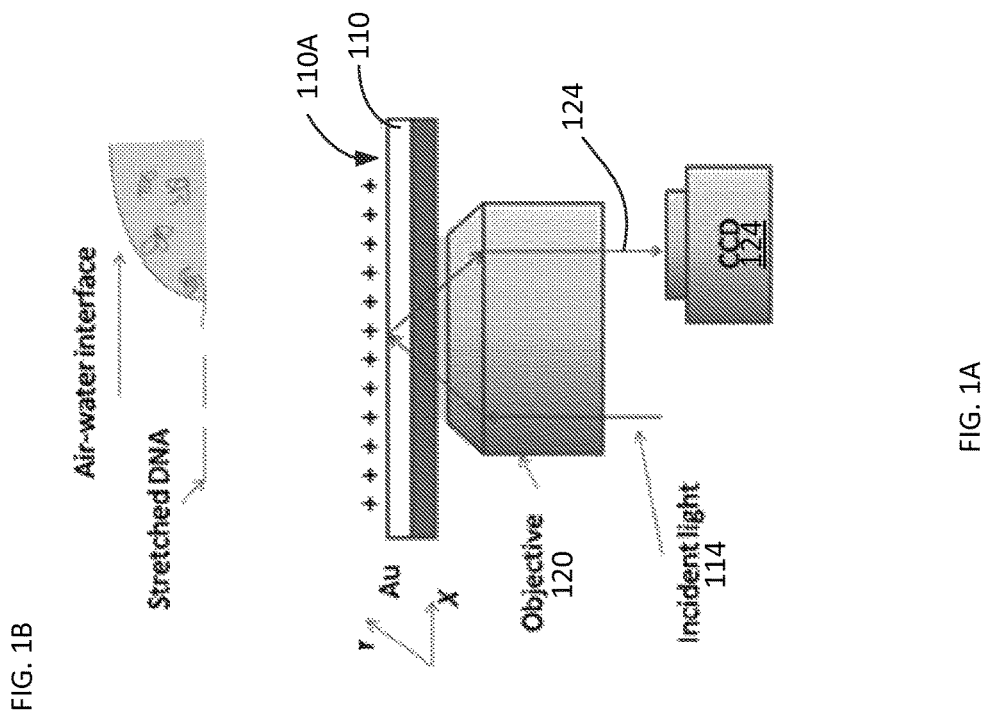

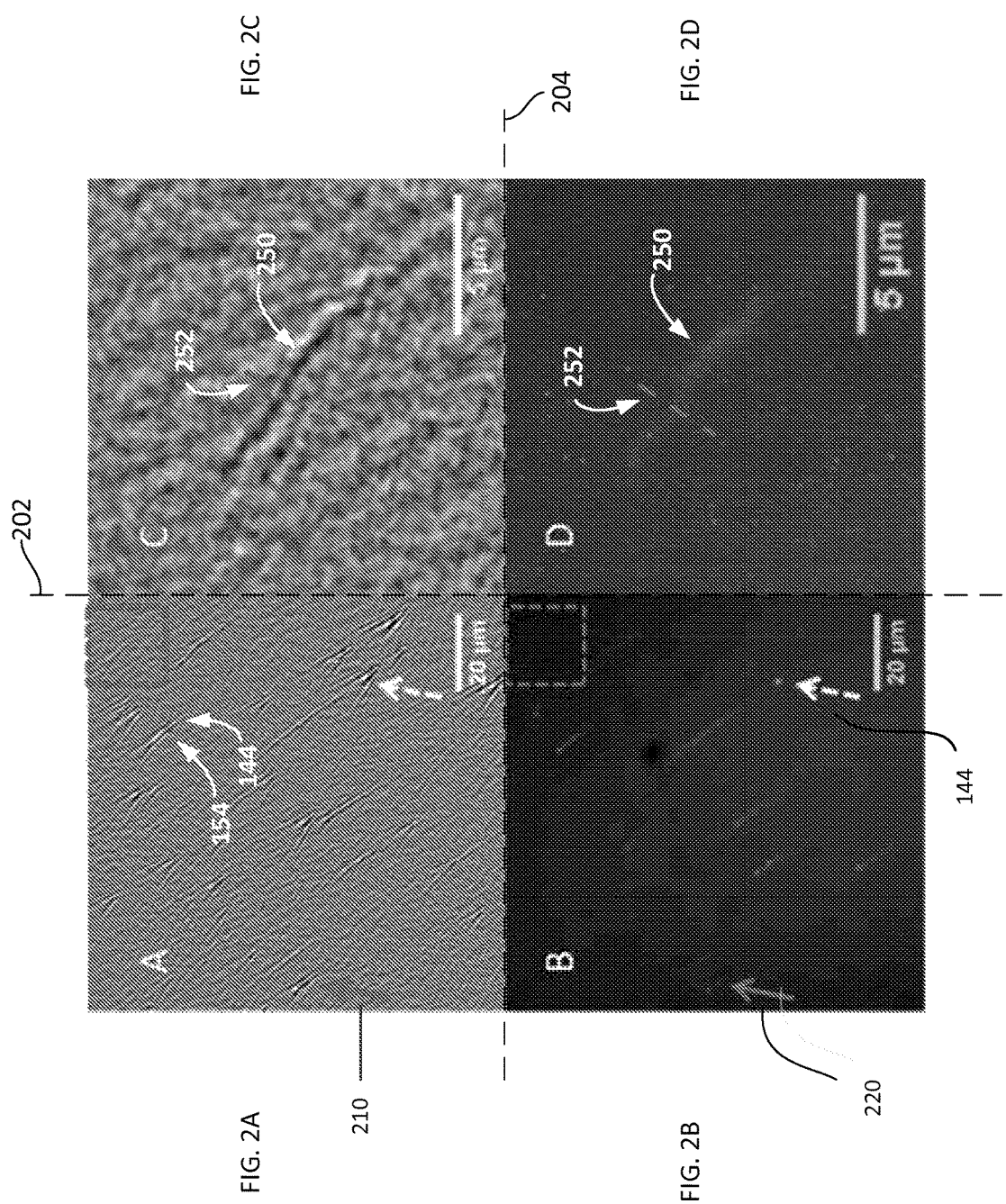

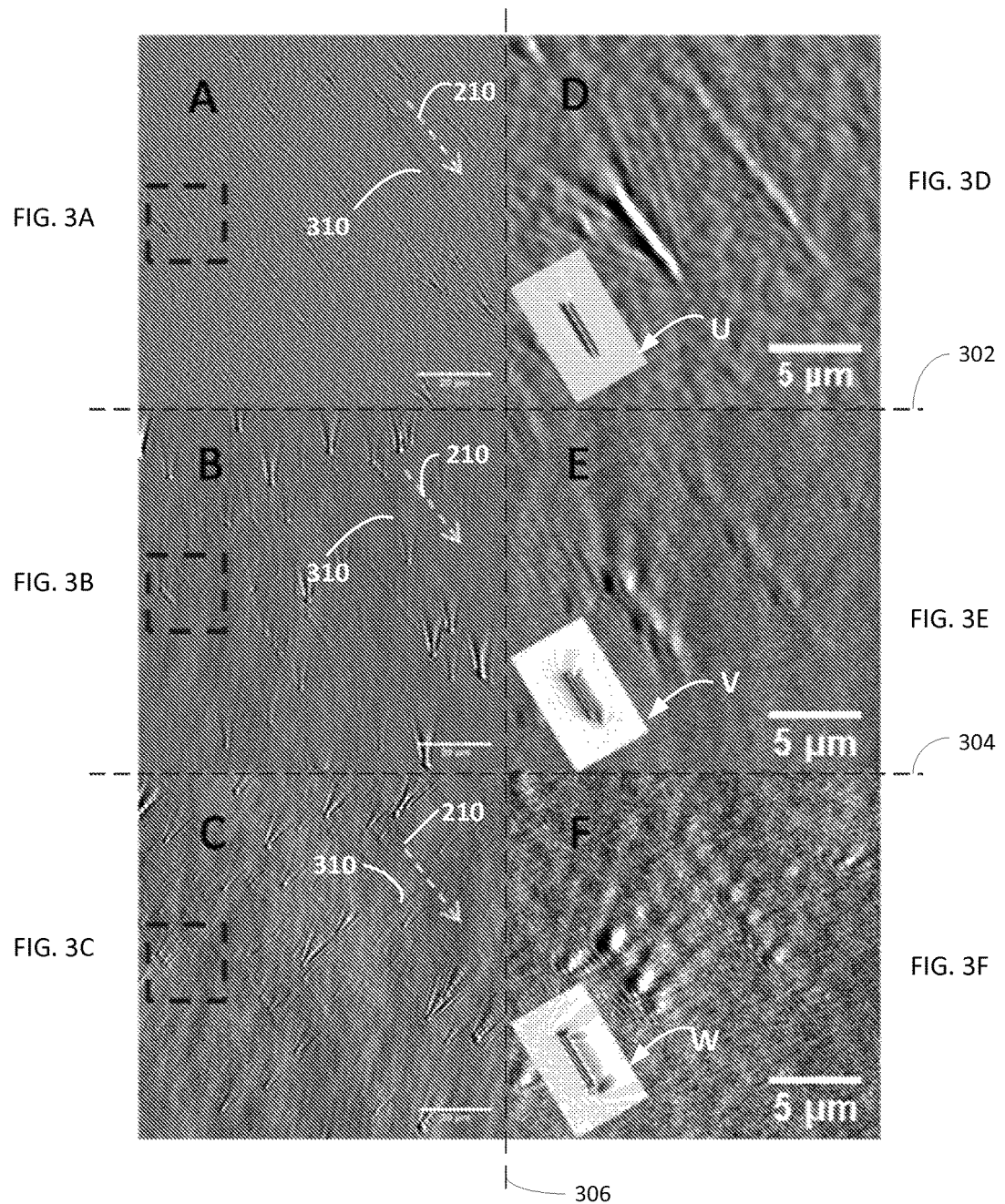

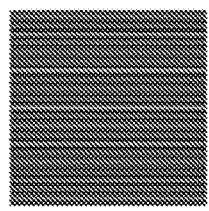
FIG. 6A(1)
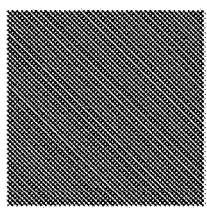
FIG. 6A(2)
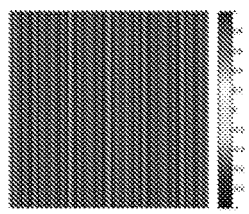
FIG. 6A(3)
Cylindrical Wave
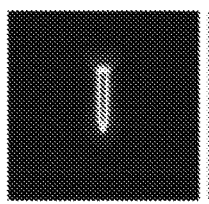
FIG. 6B(1)
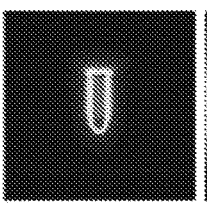
FIG. 6B(2)
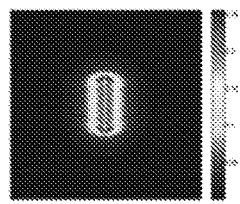
FIG. 6B(3)
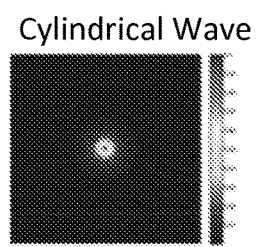
FIG. 6B(4)
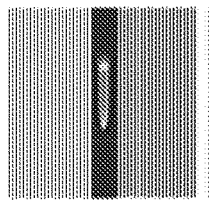
FIG. 6C(1)
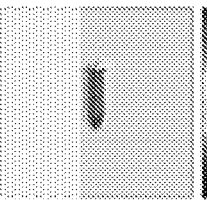
FIG. 6C(2)
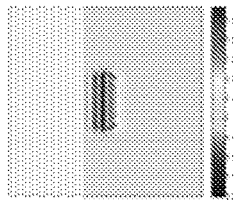
FIG. 6C(3)
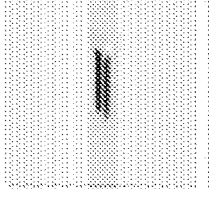
FIG. 6D(1)
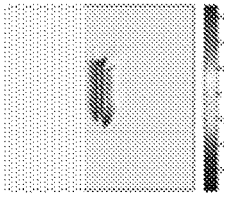
FIG. 6D(2)
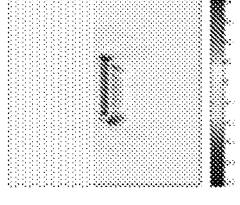
FIG. 6D(3)

PSF

Deconvolved image

Original image

PLASMONIC IMAGING AND DETECTION OF SINGLE DNA MOLECULES

CROSS-REFERENCE TO RELATED APPLICATIONS

This patent application represents the national stage entry of PCT International Application No. PCT/US2015/010018 filed on Jan. 2, 2015 and claims priority from and benefit of the U.S. Provisional Patent Application No. 61/923,477 filed on Jan. 3, 2014 and titled "Plasmonic Imaging and Detection of Single DNA Molecules." The disclosure of the above-identified patent document is incorporated herein by reference.

BACKGROUND

Optical microscopy has become an indispensable tool in research, clinical and industry labs. Contrast of imaging of optically transparent samples is limited when such imaging is carried out with traditional optical microscopy. To enhance imaging contrast, various strategies including fluorescence labeling have been developed. In comparison with imaging utilizing traditional optical microscopy, fluorescence imaging requires additional sample-preparation steps, which may distort the natural properties of the molecules of the object being imaged. Fluorescence imaging is also subject to blinking and photobleaching, which shortcomings make it difficult to quantify the image intensity and study single molecules over a long time. The term "blinking" as used herein refers to the phenomenon of random switching between ON (bright) and OFF (dark) states of lights emitters (such as, for example, molecular fluorophores, or colloidal quantum dots) associated with the object under the condition of continuous excitation. In addition, due to relatively weak fluorescence emission, the speed of the fluorescence imaging procedure is relatively slow, which is not suitable for imaging of fast biological processes.

The ability of imaging or otherwise visualizing single DNA molecules is critical for studying the biophysical and biochemical properties of DNA and for developing various applications utilizing such properties (such as, for example, sequencing DNA and studying DNA-protein interactions). An important example of such applications is a technique for obtaining, with the use of optical mapping, high-resolution genome-wide restriction maps of single DNA molecules (discussed, for example, by Teague, et al., in High-resolution human genome structure by single-molecule analysis. *Proc Natl Acad Sci USA,* 2010 107(24):10848-10853, which publication is incorporated by reference herein). The resulting maps serve as a "barcode" or "finger print" for the sequence of an unknown DNA of an organism. The current approach to the above-identified optical mapping relies on fluorescence microscopy, during which labeling of DNA with fluorescent dyes (such as YOYO-1, for example) is found to elongate and twist the native structure of the DNA, and affect the charge distribution of DNA. The optical mapping technique that is devoid of (or does not require) labeling DNA with fluorescent dye (a label-free technique) would facilitate the elimination of these effects, and provide additional information because such technique would facilitate measurement of the intrinsic physical characteristics of DNA instead of those of the labels. As used herein, the term "label-free technique" refers to a process of detection without the need to covalently attach a fluorophore to the molecule being detected (such as a protein or nucleic acid, for example). The atomic force microscopy (AFM) is a powerful label-free technique for imaging single DNA molecules, but it is operationally slow (taking seconds to minutes to acquire a single image). Additionally, the scanning of the AFM probe may perturb the DNA samples.

Surface plasmon resonance is another example of a label-free technique, which has been used to study molecular bindings. Recently, imaging of single viruses with high-resolution surface plasmon resonance microscopy has been demonstrated by Applicants (Wang, et al., Label-free imaging, detection, and mass measurement of single viruses by surface plasmon resonance. *Proc Natl Acad Sci USA* 107 (37): 16028-16032, 2010). Despite of the advances, it remains a difficult challenge to image single molecules, such as DNA, proteins or any other biomolecules or macromolecules with surface plasmon resonance microscopy. A primary reason is the background noise associated with the surface plasmon resonance microscope, including interference patterns arising from the coherence of light, dirt on and imperfection of the optical components, including objective and light sources, and non-uniform distribution of the light illumination. The present invention discloses a differential imaging method and apparatus aiming at removing the background noise, thus allowing for label-free imaging of biological molecules.

SUMMARY

In one embodiment, the present invention is a method of label-free imaging of single biomolecule, macromolecule, or other molecules with a differential surface plasmon resonance technique (DSPR). The plasmons may be created optically at the surface of a metal film, and the prorogating plasmonic waves are scattered by the sample molecules on the surface, creating a plasmonic image with contrast many orders of magnitude greater than the conventional bright field optical microscopy image. Noises and unwanted interference patterns from the optical system may be removed with the differential method, which further enhances the image contrast and make it possible to image and detect single molecules such as DNA or proteins.

In one embodiment, the present invention discloses a method of detecting and imaging a single molecule. The method comprises the steps of illuminating a single molecule, that has been stretched and aligned along a first direction on a metal surface, and the metal surface with electromagnetic radiation to create a plasmon wave propagating at the metal surface such that scattering of said plasmon wave by the single molecule forms scattered light; acquiring the scattered light with an optical detector; and producing an image of the single molecule with a differential surface plasmon resonance technique.

In one embodiment, the present invention discloses an apparatus for detecting and imaging a single molecule in a sample. The apparatus comprises a metal surface on which the single molecule is stretched and aligned; a light source illuminating the metal surface and the single molecule; an optical device disposed to gather and spectrally analyze light scattered from a single molecule that has been stretch and aligned on the metal surface along the first direction; and electronic circuitry operable to produce an image of the single molecule based on a differential surface plasmon resonance technique.

BRIEF DESCRIPTION OF DRAWINGS

The idea of the present invention is better understood with reference to the following generally not-to-scale Drawings, of which:

FIGS. 1A, 1B, 1C, 1D, and 1E are diagrams and images providing a schematic illustration of the differential surface plasmon resonance (DSPR) system and its operation as applied to DNA imaging according to the idea of the present invention. FIG. 1A: DSPR system; FIG. 1B: at least one λ-DNA molecule is stretched on a modified gold surface; FIG. 1C: a scheme of functional connection(s) between the present compositions of matter; FIG. 1D: an SPR image; FIG. 1E: a DSPR image. One embodiment of DSPR involves a lateral translation of the sample stage, and subtraction of images acquired before and after the lateral translation of the sample stage to produce a differential image.

FIGS. 2A, 2B, 2C, 2D, 2E, and 2F provide a set of images and graphs showing images of stretched λ-DNA molecules on the surface of gold. FIGS. 2A and 2B are typical DSPR and fluorescent images of DNA molecules; FIGS. 2C and 2D are the magnified portions of the images of single DNA molecule indicated by square areas; FIG. 2E is fluorescent and DSPR intensity profile at the same location on single DNA molecule in FIGS. 2C and 2D; FIG. 2F is the histogram of the DSPR intensities and Gaussian fitting results of DNA molecules; Inset depicts a typical DSPR intensity profile of single DNA molecule and dimmers; Arrows 210 in FIGS. 2A and 2B show the directions of stretching the molecule.

FIGS. 3A, 3B, 3C, 3D, 3E, 3F, 3G, 3H, and 3I are images and graphs showing DSPR images procured with an embodiment of the invention while the surface plasmonic wave propagated along the metal surface along the following directions. FIG. 3A: the direction 310 of propagation of the surface plasmonic wave propagation is parallel with the direction 210 of stretching and aligning of λ-DNA molecules; FIG. 3B: the direction 310 of surface plasmonic wave propagation is at 45° with respect to the direction 210 of stretching and aligning of λ-DNA molecules; FIG. 3C: the direction 310 of surface plasmonic wave propagation is perpendicular to the direction 210 of stretching and aligning of λ-DNA molecules; FIGS. 3D, 3E and 3F provide enlarged imaged of the portions of FIGS. 3A, 3B, 3C outlined as squares; FIGS. 3G, 3H, and 3I are the cross-section intensity profiles corresponding to simulated and experimental SPR images of FIGS. 3A and 3D, FIGS. 3B and 3E, and 3C and 3F, respectively. The dashed yellow arrows 210 and solid red arrows 310, 320, 330 indicate the directions of molecule stretching and the directions of surface plasmonic wave propagation, respectively.

FIG. 4A presents a deconvolved DSPR image of the DNA molecules in the large area. FIG. 4B presents an Image of one DNA molecule after the procedure of deconvolution. FIG. 4C presents the same DNA molecule as that in FIG. 4B before deconvolution. FIG. 4D illustrates length distribution of stretched λ-DNA molecules measured by the DSPR imaging method according to an embodiment of the invention, and the Gaussian fitting results. See Example for details in image deconvolution method.

FIG. 5A is a flow-chart schematically outlining a procedure of optical mapping with DSPR imaging, while FIG. 5B provides corresponding pictorial illustrations. FIG. 5C presents a restriction map of λ-DNA by Sma I restriction endonuclease and the DSPR image of DNA fragments after digestion. Cutting sites were provided by the manufacturer (New England Biolab Inc.).

FIGS. 6A(1), 6A(2), 6A(3), 6B(1), 6B(2), 6B(3), 6B(4), 6C(1), 6C(2), 6C(3), and 6D(1), 6D(2), 6D(3) provide a set of images including the DSPR images that were simulated as the scattering of propagating surface plasmon (SP) wave by DNA molecules. FIGS. 6A(1) through 6A(3) show real part of the propagating surface plasmon (SP) wave, simulated as a plane wave propagating in different directions. FIGS. 6B(1) through 6B(4) show amplitude of the wave scattered by the stretched DNA molecule, simulated by the superposition of a set of cylindrical waves. Different object waves (FIGS. 6B(1) through 6B(3)) are due to a phase correction introduced relative to SP wave propagating direction. FIGS. 6C(1) through 6C(3) show amplitude of the SPR images after superposition of the SP wave [FIG. 6A(1) through FIG. 6A(3)] and object wave [FIG. 6B(1) through FIG. 6B(3), respectively] FIGS. 6D(1) through 6D(3) show DSPR images, simulated by shifting the SPR images (FIG. 6C(1) through FIG. 6C(3)) by several pixels and subtracting the resulting images from the original images to obtain differential images, in which the background noise is greatly reduced and, therefore, the imaging sensitivity and signal noise ratio is increased.

FIG. 7A shows real part of the propagating SP wave, simulated as a planar wave propagating in different directions. FIG. 7B shows amplitude of the object wave (that is defined as a wave scattered by the object, such as a molecule stretched on the metallic surface), simulated by the superposition of a set of cylindrical waves. Different object waves are due to a phase correction introduced relative to SP wave propagating direction. FIG. 7C shows amplitude of the SPR images after superposition of the SP wave and object wave. FIG. 7D shows a graph corresponding to DSPR image, simulated by shifting the SPR image (of FIG. 1D) by several pixels and subtraction from the original image.

DESCRIPTION

Figures 2E, 2F:
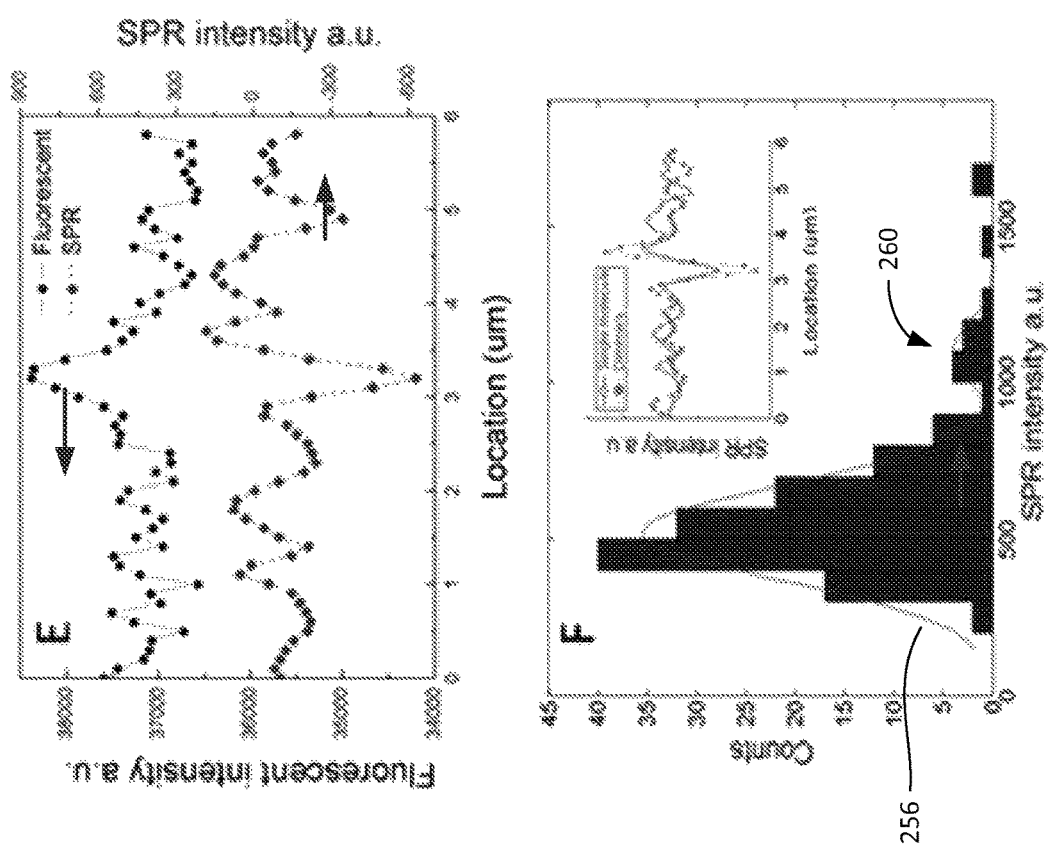

Implementations of the present invention are directed to developing an imaging technique that is fast (less than a millisecond per image taken) and that can be practically integrated with micro- and nano-fluidic devices. Embodiments of the present invention are useful for high throughput optical mapping of biomolecules, e.g., DNAs.

As used herein, the term "surface plasmon resonance" (SPR) refers to the collective oscillation of electrons, in a solid or liquid, that has been stimulated or caused by the incident light. The resonance condition is established when the frequency of light photons matches the natural frequency of surface electrons oscillating against the restoring force of positive nuclei. SPR in nanometer-sized structures is sometimes referred to as localized surface plasmon resonance.

The embodiments of the present invention are directed to a method for detecting and imaging of a single molecule, and are generally applicable to detecting and imaging of molecules, such as biological molecules and polymer molecules.

In one embodiment, the target molecule may be selected, for example, from proteins, peptides, polypeptides, enzymes, protein-DNA complexes, polynucleotides, antibodies, DNAs, RNAs, siRNAs, antigens, antigenic epitopes and variants thereof, hormones, carbohydrates, lipids, phospholipids and biotinylated probes. A target molecule may also comprise antisense RNA, RNAi, snRNA, miRNA, or cDNA or other types of biopolymers. A target nucleic acid may also comprise nucleic acid analogs. In one specific embodiment, the biomolecule is a DNA.

FIGS. 1A, 1B, 1C, 1D, 1E schematically illustrate the principles of the present DSPR approach. Incident light is directed, at an angle of incidence, onto a metallic film carrying a molecule in question; optical image of the metallic film with the molecule is formed in light reflected off of the metallic film. When the angle of incidence is tuned to a judiciously chosen value, surface plasmonic waves are excited at propagate along the surface of the film. When the energy of the incident light is transferred to the plasmonic wave(s), the intensity of the image formed in the reflected light is reduced. When a macro object is present on the metallic surface, it scatters the plasmonic waves and creates a high contrast image. However, the contrast of such image is not high enough to image an object that includes only a single DNA molecule on the metallic film. The DSPR method employs, the improvement of the image contrast by reducing background noises and interference patterns in the resulting image formed with the light scattered at the single molecule.

In particular, and in reference to FIG. 1A, in practice, in order to detect and image a single molecule with the use of the above method, a metal surface 110 is employed to support the molecule at hand. Applicable metal surfaces may include any of metals or alloys capable of producing surface plasmon resonance such as gold, silver, copper, aluminum, magnesium, platinum, palladium, cobalt, chromium, nickel, and a composite made of two or more of these metals. In one specific embodiment, the preferred metal surface is selected from at least one of gold, silver, platinum, because these metals are chemically inert and surface plasmon resonance condition can be created with light.

Copper, aluminum and other metals may also be used for this purpose, although they are less inert than gold, silver and platinum.

As illustrated in FIG. 1C, the metallic substrate 110 having a metallic surface 110A may be optionally modified to include functional groups, such as —NH2 or —SH. Through these functional groups, the molecules to be detected may be attached to the metal surface.

Biomolecules, such as DNAs, are geometrically anisotropic. Therefore, it is appreciated that, the scattering of the plasmonic wave propagating along the surface 110A by a biomolecule (e.g., a DNA) depends on the orientation of the biomolecule relative to the plasmonic wave propagation direction. To detect and image a single molecule, the single molecule may be stretched and aligned along a chosen direction on the metal surface 110A.

Various methods may be used to stretch and align molecules in a chosen direction on the metal surface. In one specific embodiment, illustrated in FIG. 1B, a receding air-water interface may be employed. Specifically, the metal surface 110A are initially modified include functional groups. The molecules, such as DNA molecules, that have been attached to the functional groups (such as —NH2 or —SH) with which the surface 110 has been modified, are restored to their linear forms by heating the surface 110A to, for example, 65° C. for 10 min, followed by quick cooling in ice-water bath, according to the manufacturer's instruction.

Thereafter, the λ-DNA molecules may be then stretched by the surface force of a moving air-water interface using, for example, a method by Ma Y. et al., in "Polyaniline nanowires on Si surface fabricated with DNA templates", *J. Am. Chem. Soc.* 126(22): 7097-7101 (2004). Specifically, a 2 µL drop of λ-DNA (5-50 ng/mL, in 1×TE buffer, pH 8.0) solution may be deposited onto the edge of a clean glass coverslip, and carefully placed as a drop onto the top of the SH-PEG-NH$_2$ modified metal surface. The drop may spread immediately as the cover glass and the gold are sealed together. After a few minute delay, the cover glass may be slid away and the metal surface may be rinsed with de-ionized water thoroughly and blown dried with nitrogen gas.

Considering a single, individual molecule that has been stretched and aligned on the metal surface, the single molecule and the metal surface are illuminated with electromagnetic radiation from, for example, a super luminescence diode, light emitting diodes, laser source, or even a more traditionally used lamp such as mercury arc lamp or halogen lamp. Caused by such irradiation, the plasmon waves (plasmons) are created on and propagate along the metal surface to be scattered by the single molecule at hand.

Incident light 114 may be directed onto a metal surface via an optical microscope objective 120. The optical microscope objective may have either a low or a high numerical aperture. In one specific embodiment, the optical microscope objective may be a high numerical aperture (NA) oil immersion objective (in one example, NA=1.49). A high numerical aperture objective is preferred because its field of view (FOV) covers a wide range of angles at which light is incident onto the surface. The diversity of such multiple angles of incidence ensures that there exists at least one value of the angle of incidence at which a surface plasmon wave is excited at and propagates along the surface.

When an object (such as a single molecule) is present on the surface 110A, it may scatter the generated plasmonic waves, producing scattered light that is further collected to generate a contrast image representing the surface with an object thereon.

IN particular, when the excitation of the SP occurs, the portion 124 of the incident light 114 that has been scattered from the surface has the lowest intensity (as the partial energy of the incident light is transferred to the plasmonic waves). In one embodiment, the angle of incidence of light from the objective 120 onto the surface 110A may be adjusted by equipping the metallic substrate with a motorized translation stage or another device (not shown) programmed to reposition the substrate in angular space. In one implementation, the scattered light 124 may be collected by using the same optical microscope objective 120 and directed to an optical detector 130. Devices such as CMOS and CCD imagers may be used to record the SPR microscopy images. Applicants found that although some objects (such as viruses and nanoparticles) may be successfully detected and imaged, imaging a single biomolecule (such as a DNA molecule) remains difficult because the large background noise arising from various sources, including interference patterns from the coherence of light, dirt on and imperfection of the optical components, including objective and light sources, and non-uniform distribution of the light illumination In order to image single molecules or objects that scatter plasmonic waves weakly, the background noise must be reduced. This may be achieved with a differential method disclosed below.

In one embodiment, an image of the single molecule may be produced by using a differential surface plasmon resonance technique referred to herein as DSPR. Noise and unwanted interference patterns formed at the surface of the detector 130 (in part, by the optical imaging system) are removed with the DSPR method, which further enhances the image contrast and make it possible to image and detect single molecules, such as DNA molecules.

According to the idea of the DSPR technique, and in further reference to FIG. 1A, the sample of a single molecule may be translated laterally (along the surface 110A, in at least one of the x- and y-directions) back and forth between two positions, at each of which an image is recorded in scattered light 124 (aggregately, two images are recorded at the two positions). For example, one of the images may be recorded at a first position chosen such as to include the sample of the single molecule and background noise at the surface 110A. The other image may be recorded at a second position where the position of the sample of the single molecule is shifted relative to the objective of the microscope, but the background noise remains the same. The first and second positions on the surface 110A are defined such as to be characterized by the same optical environment (with an exception of the position of the molecule at the first position). The term 'optical environment' refers to any or a combination of the light illumination used, optical components employed in the system, and optical detection (CCD or CMOS imager, for example).

According to the proposed DSPR technique, a differential image is obtained by subtracting one image from another image (for example, by subtracting the first image from the second image) to remove all the noises and interference patterns of the entire optical system other than the sample itself, leading to superior image contrast.

The principle of DSPR techniques may be illustrated with the following equations. The first image (obtained before the translation of the substrate 110) may be denoted as I(x,y) according to Equation 1, $$I(x,y) = I_S(x,y) + I_B(x,y), \quad (1),$$

where $I_S(x,y)$ is the irradiance of the SPR image of the sample (a single molecule), and $I_B(x,y)$ is the background irradiance in the image present due to all sources unrelated to the sample. For weak scatterers of the plasmonic waves (such as DNA), the value of $I_S$ is small and overwhelmed by the value of $I_B$. The second image, obtained after the translation of the substrate 110 by $\Delta x$, for example, may be expressed as $$I'(x,y) = I_S(x,y) + I_B(x+\Delta x,y), \quad (2),$$

and the irradiance DI of the differential SPR (DSPR) image is expressed as $$DI(x,y) = I'(x,y) - I(x,y) = \left(\frac{dI_S}{dx}\right)\Delta x, \quad (3).$$

Equation 3 employs a spatial derivative of the irradiance distribution of the sample image along the x-direction. By using Equations (1) through (3), the background irradiance corresponding to the image is removed. Therefore, a single molecule (such as the DNA molecule) may be detected and the image of the single molecule may be produced.

In further reference to FIGS. 1A, 1B, 1C, and 1D, It is understood that embodiments of the present invention additionally include an apparatus for detecting and imaging of a single molecule on a supporting surface. The present apparatus may be used to detect any single molecules as discussed above, such as single biomolecules (DNAs, proteins, et al.), or macromolecules (polymers, liposomes, et al.).

The apparatus includes a metal surface on which the single molecule is stretched and aligned; a light source configured to illuminate the metal surface and the single molecule at hand; an optical imaging system (including an optical detector and first programmable electronic circuitry, such as a computer processor, not shown) configured to gather and spectrally analyze the light scattered from/by the single molecule; as well as second electronic circuitry operable for producing an image of the single molecule based on a differential surface plasmon resonance technique. In one example, the optical imaging system may include a microscope such as, for example, an inverted microscope (such as Olympus IX81).

An embodiment of the apparatus may include an image-recording device such as a photo- or video-camera. In one specific embodiment, the present apparatus uses a CMOS camera (ORCA-Flash 4.0 from Hamamatsu, Japan) for recording the SPRM image.

Further, the present apparatus may also comprise adjustable transitional stages. For example, a motorized translation stage may be used to adjust the incident angle of the light. A motorized XY stage may also be incorporated on the microscope to translate the metal surface and the stretched single molecules.

The first and/or second electronic circuitry may be further linked to a processor such as any appropriate type of graphic processing unit (GPU), general-purpose microprocessor, digital signal processor (DSP) or microcontroller, and application specific integrated circuit (ASIC), and the like.

The processor may execute computer program instructions to perform various processes associated with the detection and imaging of single molecules as discussed above and following hereafter. For example, the processor may execute the differential surface plasmon resonance technique as discussed above to increase the image contrast. Two SPR images may be recorded before and after laterally moving the metal surface and the stretched single molecule by a small distance with the motorized XY stage, and the differential image may be produced by the processor. The differential image may be used as the resulting DSPR image to increase the image contrast and sensitivity.

In one embodiment, the present apparatus and method provide a fast and label-free ways for single molecule detection. Previously reported DNA imaging techniques were mostly based on fluorescence labeling, which is difficult to quantify the image intensity and study single molecules over a long time due to blinking and bleaching. As shown in FIGS. 2A, 2B, 2C, 2D (which are separated by dashed lines 202, 204 for better readability) and 2E, 2F, the present apparatus allows imaging of single DNA molecules for the first time without using fluorescence labeling. Further, the DSPR images in the present invention may be acquired at an exposure time of 3 ms, with a 256×256 µm full field of, which are free of blinking or photobleaching effects. In contrast, a much longer exposure time of 0.5-1 s was required to acquire a high quality fluorescence image with the same field of view. The exposure time of DSPR images can be further shortened using faster cameras. This high temporal resolution in the present invention is important for studying fast processes.

Further, FWHMs (Full-Widths Half-Maximum) were found to be ~300 nm for both the present DSPR imaging method and fluorescence image plots, which is close to the diffraction limit of the optical system (with the theoretical value of about 230 nm). It was observed that the fluorescent image contrast blinked and decreased over time due to photobleaching effect, while the DSPR image contrast is highly stable and last for hours.

Unlike fluorescent images, the DSPR image contrast in the present apparatus and method measures the intrinsic mass density distribution of DNA molecules since the scattered plasmonic wave is proportional to local optical mass density, which provides quantitative information about the sample molecules.

The DSPR imaging technique of the present invention is label-free, fast, and quantitative and compatible with micro- and nano-fluidic devices, which are attractive for high throughput optical mapping of single biomolecules such as DNAs.

EXAMPLES

Materials used in experiments included λ-DNA (cIind 1 ts857 Sam 7) (48,502 bp), TE buffer (1×, pH 8.0), and Sma I digestion enzyme from Invitrogen (Carlsbad, Calif.); YOYO-1 dye (1 mM in DMSO) from Molecular Probes (Eugene, Oreg.). Thiol-PEG-Amine (HS-PEG-NH$_2$, MW 1000) from Nanocs (Boston, Mass.), and 2-mercaptoethanol from Gibco (Grand Island, N.Y.).

Surface Modification.

The SPR substrate 110 included BK7 glass cover slips (from VWR, www.vwr.com) coated with 2 nm thick layer of chromium and then with a 47 nm thick layer of gold. The gold surface 110A (of FIG. 1A) was covered with a SH-PEG-NH$_2$ self-assembled monolayer. Each resulting substrate chip was rinsed with de-ionized water and ethanol, and then blown dry with nitrogen gas. The chip was then further cleaned with hydrogen flame and immediately submerged in 0.5 mM HS-PEG-NH$_2$ water/ethanol (1:1) solution. After left in the solution for 24 h in the dark, the chip was taken out of the solution and rinsed with de-ionized water and ethanol, and then blown dry with nitrogen gas.

Fixation of a DNA Molecule(s).

Stretching DNA on coated gold surface: Before stretching, the λ-DNA molecule was restored to its linear form by heating to 65° C. for 10 min followed by quick cooling in ice-water bath, according to the manufacturer's instructions (https://tools.lifetechnologies.com/content/sfs/manuals/Lambda_DNA_man.pdf). The λ-DNA molecule was stretched by the capillary force of a moving air-water interface, using a similar method as molecular combing. A 2 µL drop of λ-DNA (5-50 ng/mL, in 1×TE buffer, pH 8.0) solution was deposited onto the edge of a clean glass coverslip, and carefully placed onto the top of the SH-PEG-NH$_2$ modified gold surface. The drop spread immediately as the cover glass and the gold sealed together. After about a 2 minutes grace period, the cover glass was slid away and the gold surface was rinsed with de-ionized water thoroughly and blown dried with nitrogen gas.

A DSPR Setup.

The DSPR system of FIG. 1A was based on the Kretschmann configuration (see Kretschmann, 1971, Die Bestimmungoptischerkonstanten von metallendurchanregung von oberflachenplasmaschwingungen. *Z Phys* 241:313-324) using a high numerical aperture oil immersion objective (NA=1.49) and an inverted microscope (Olympus IX81), an approach similar to that used by Huang et al. [Huang, et al., Surface plasmon resonance imaging using a high numerical aperture microscope objective. *Anal Chem* 79(7):2979-2983]. The SPR chip 110 was placed on the objective 120 with index-matching liquid. A free-space super luminescence diode (from SUPERLUM, Ireland) configured to generate 680 nm 15 mW p-polarized light was used as the light source (not shown). The angle of incidence of light 114 was adjustable by employing a motorized translation stage (Thorlabs, Newton, N.J.; not shown)). A CMOS camera 130 (ORCA-Flash 4.0 from Hamamatsu, Japan) was used with the system for recording the SPRM image. A motorized XY stage (Ludl Electronic Products Ltd., Hawthorne, N.Y.; not shown) was incorporated on the microscope to translate the sensor chip 130. This system is configured to obtain high-resolution distortion-free images with diffraction-limited spatial resolution in the transverse direction and near diffraction-limited spatial resolution along the plasmonic wave propagation direction.

DSPR Imaging.

The angle of incidence of light beam 114 onto the surface 110A was adjusted to the surface plasmon resonance angle at which the irradiance of scattered light imaged by the camera 130 reaches the minimum. A direction of the surface plasmonic wave propagation was tunable (modifiable) in response to the built-in means configured to change the direction of incident light 114 with respect to the surface 110A. The sampling rate of the image-acquisition process was set at 3 ms/frame with the Hamamatsu camera. Two SPR images were recorded (before and after the lateral movement of the sensor chip by a small distance with the motorized XY stage), and the differential image was formed as the resulting DSPR image to increase the image contrast (sensitivity), as discussed above.

Fluorescent Imaging.

After imaging with the DSPR modality of the present invention, the stretched λ-DNA molecule was stained with YOYO-1 fluorochrome (300 nM in TE buffer containing 20% 2-mercaptoethanol, pH 8.0) for 2 hour in the dark. Fluorescent images were taken in imaging buffer (100 nM in TE buffer containing 20% 2-mercaptoethanol, pH 8.0), using the mercury lamp with a filter set of 450±50 illumination band and 510±50 emission band. The exposure time was chosen to be 0.5-1 s to maximize the signal-to-noise ratio.

Restriction of the Endonuclease Digestion of DNA.

Surface-stretched DNA molecules were digested with the 40 µL of 1× restriction buffer that contained 10-20 units Sma I restriction endonuclease. The surface was incubated in a humidified chamber for 1 hour at 30° C. After digestion, the overlaying buffer was removed and the chip 110 with the molecule was rinsed with de-ionized water.

Results and Discussion

Differential Surface Plasmon Resonance Imaging.

The advantageous contrast enhancement is illustrated in FIGS. 1D and 1E, by comparing the images of 80 nm platinum nanoparticles obtained with the presently disclosure DSPR approach (image 144, FIG. 1E) and the conventional SPR approach (image 148, FIG. 1D). The conventional SPR cannot resolve the individual nanoparticles clearly, but the DPSR clearly reveals each nanoparticle as a bright spot (marked as 150) with a long "tail" 154, caused by plasmonic scattering of the nanoparticles.

DSPR Images of DNA Molecules.

For optical mapping, it is necessary to stretch the individual DNA molecules. In the present work, double-strand λ-DNA molecules were stretched on a gold surface modified with NH-PEG-NH$_2$ (MW 1000) by a receding air-water interface method (as shown in Bensimon, et al., (1994) Alignment and sensitive detection of DNA by a moving interface. Science 265(5181):2096-2098). After imaging the DNA molecules with DSPR, the molecules were labeled with YOYO-1 and imaged with fluorescence microscopy. FIGS. 2A and 2B show, respectively, a typical DSPR image (similar to that of FIG. 1E) and a fluorescent image of individual λ-DNA molecules. Stretched DNA molecules (indicated with solid arrows 210) were imaged as lines with "tails" 154 in the DSPR image. The "tail" portions 154 of the DSPR image are due to the scattering the plasmonic wave propagating along the surface at the DNA molecules. The DSPR and fluorescence images of the same sample are in excellent agreement with each other (see FIGS. 2A, 2B, 2C, 2D, 2E, and 2F). The contour length of single λ-DNA molecules as revealed by DSPR is ~17 µm, which is consistent with the value obtained from fluorescence microscopy. Some of DNA molecules are coiled (dashed yellow arrows), which appeared as bright spots in the fluorescence image. In contrast, the coiled DNA molecules appeared as pairs of dark and bright spots with "tails" in the DSPR images.

The DSPR images were acquired at an exposure time of 3 ms with a 256×256 µm full field of view, which are free of blinking or photobleaching effects. In contrast, an exposure time of 0.5 sec to about 1 sec was required to acquire a high quality fluorescence image with the same field of view. Note that the exposure time of DSPR images can be further shortened using faster cameras. This high temporal resolution is important for studying fast processes.

DSPR Intensity of Single DNA Molecules.

FIGS. 2C and 2D are the enlarged portions of the DSPR and fluorescence images of a stretched DNA molecule shown in FIGS. 2A and 2B. It is notable that the curved shape of the DNA molecule 250 was revealed by both the DSPR and fluorescence images. Cross-sectional intensity profiles of the DNA molecule 250, taken along the dotted line 252, were plotted in FIG. 2E. The FWHMs values were found to be ~300 nm for both the DSPR and fluorescence image plots, which is close to the diffraction limit of the optical system (230 nm theoretically). The SNR (signal-to-noise ratios) of the DSPR image is higher than that of the fluorescent image. In addition, Applicants observed that the fluorescent image contrast blinked and decreased over time due to photobleaching effect, while the DSPR image contrast is highly stable.

Unlike in the images formed in fluorescent light, contrast of a DSPR image is a measure of the intrinsic mass density distribution of DNA molecules, which provides quantitative information about the sample molecules. The intensity distributions representing the individual DNA molecules in DSPR images were measured and presented via a histogram of FIG. 2F. This histogram can be approximately fit with a Gaussian distribution 256 having a mean intensity of 520 a.u. (x-axis of the plot 256), which measures the average mass of a single DNA molecule. A small second peak 260 appearing at the plot 256 at the mean irradiance (intensity) coordinate of 1097 a.u. (x-axis of the graph of FIG. 2F) that is twice that of the main peak may be attributed to the formation of DNA dimmers. Intensity profiles of a typical single DNA molecule and dimmers (aggregation of two DNA molecules) were plotted in the inset of FIG. 2F. The peak intensity for the dimmers is about twice of that for a single DNA molecule.

Scattering Pattern in DSPR Imaging.

Different from the isotropic nanoparticles, the DNA molecule is anisotropic. Embodiments of the present invention take advantage of this fact in exploiting the dependence of the scattering of a propagating plasmonic wave, at the DNA molecule, on the orientation of the DNA molecule relative to the plasmonic wave propagation direction.

In one embodiment, according to the idea of the present invention, the resolution in the DSPR images of a single molecule is further improved by adjusting and/or modifying the direction of propagation of the plasmonic wave relative to that along which the biomolecule of interest is oriented. In particular, contrast of the DSPR image is optimized by orienting the direction of the plasmonic wave propagation substantially parallel to the direction of orientation of the biomolecule. (In contrast, the lowest contrast of the DSPR image is demonstrated when the plasmonic waves propagation direction is perpendicular to the biomolecule orientation direction, as follows from the following empirical data.) FIGS. 3A, 3B, 3C, 3D, 3E, 3F (which are separated, for eye-guidance, with dashed lines 302, 304, 306), and FIGS. 3G, 3H, and 3I show DSPR data acquired under experimental conditions that ensured different directions of surface plasmonic wave propagation.

Figure 3G:
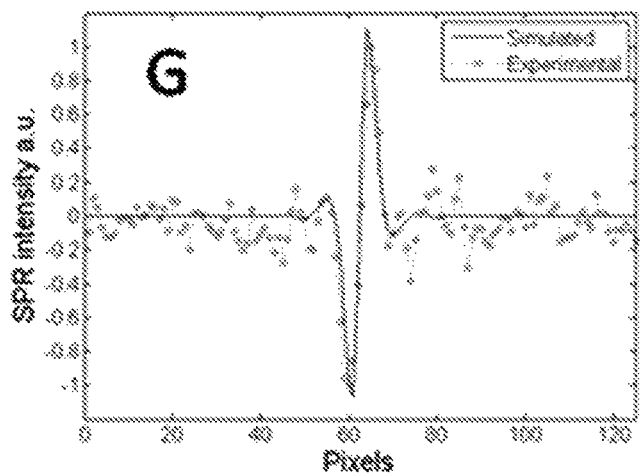
Figure 3H:
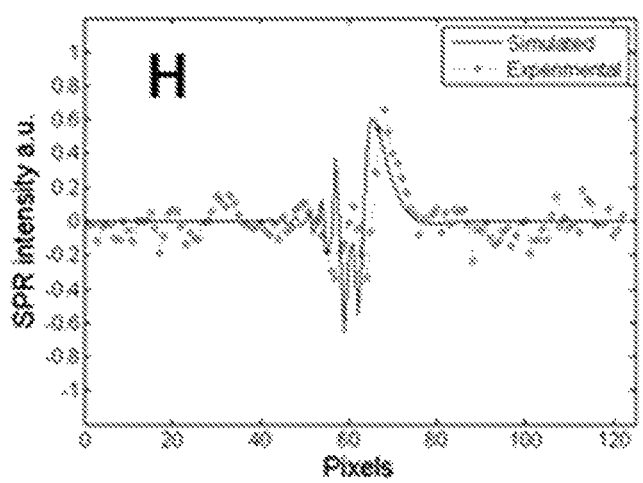
Figure 3I:
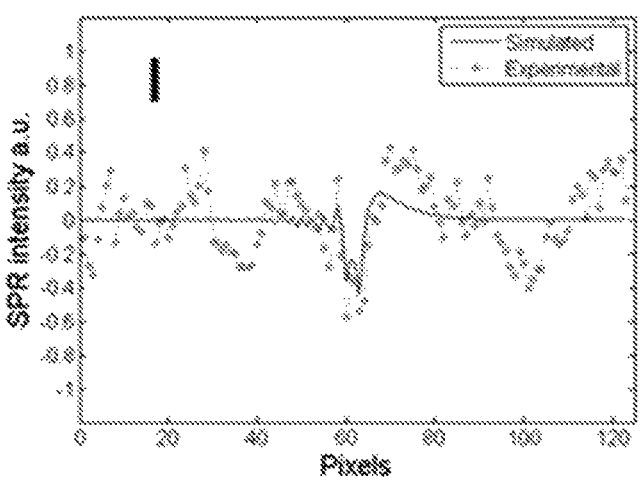

FIGS. 3A, 3B and 3C show the DSPR images of the same molecules with surface plasmonic wave (indicated by solid arrows 310) propagating along 3 different directions (parallel, inclined at 45°, and perpendicular to the direction 210 along which a DNA molecule was stretched, indicated with a dashed line), respectively. Specifically: a) FIGS. 3A and 3D provide images corresponding to the direction of surface plasmonic wave propagation being parallel to the direction of the stretching and aligning of the λ-DNA molecules; b) FIGS. 3B and 3E provide images acquired when the direction of surface plasmonic wave propagation was chosen at about 45° with respect to the direction of stretching and aligning of the λ-DNA molecules; c) FIGS. 3C and 3F provide images acquired when the direction of surface plasmonic wave propagation was substantially perpendicular to the direction of the stretching and aligning of the λ-DNA molecules. The "tail"-shape scattering patterns rotated with the change in the plasmonic wave propagation direction, which is verified by comparison of the patterns in FIGS. 3A, 3B, and 3C To better understand the scattering pattern, the DSPR images of stretched DNA molecules were modeled (as is further discussed below in reference to FIGS. 6A, 6B, 6C, and 6D). FIGS. 3D, 3E and 3F are the enlarged portions of images of the DNA molecule marked by dashed squares in FIGS. 3A, 3B and 3C, and the insets V, U, W illustrate the corresponding simulation results. The simulation reproduced the unique scattering patterns of the experimental images. The close agreement between the experimental and simulated images is more clearly shown in the corresponding cross-sectional irradiance profiles (FIGS. 3G, 3H, and 3I) corresponding to simulated and experimental DSPR images of FIGS. 3A and 3D, FIGS. 3B and 3E, and 3C and 3F, respectively.

These experimental results provide evidence that conditions of imaging of a single DNA molecule are optimized when the plasmonic waves excited in a molecule-supporting metallic surface propagates along the direction along which the biomolecule is oriented.

DNA Measurement.

The unique scattering pattern of the plasmonic waves facilitates the differentiation of the DNA molecules from other features present on the surface, but it may affect the accuracy of measuring the lengths of the molecules. To this end, an image deconvolution algorithm has been developed to remove the scattering pattern from the data representing the DSPR images of the DNA molecules. In the deconvolution algorithm, the DSPR image of a nanoparticle was used as the point spread function (PSF), and a scattering-pattern free DNA image was obtained by performing deconvolution of the original DNA image with the PSF. FIGS. 7A, 7B, 7C, and 7D illustrate pictorially the steps of the algorithm, including the recordation of a DSPR image of a single particle (such as a 40 nm platinum nanoparticle), and defining such image as the PSF; performing image deconvolution (for example, using Lucy-Richardson method in MATLAB software).

Figure 4A:
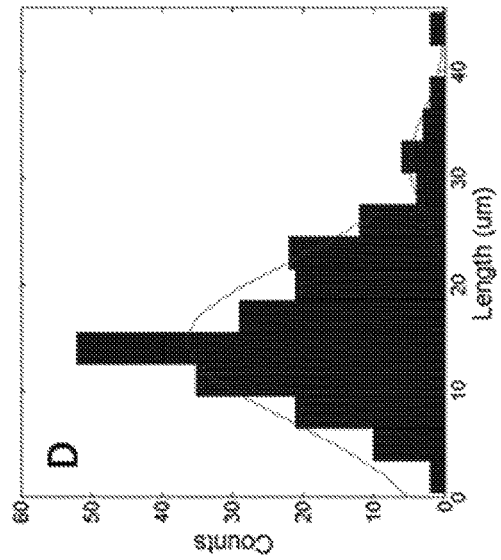
FIGS. 4A, 4B, 4C, and 4D are images and graphs showing deconvolution of images and measurement(s) of length(s) of λ-DNA molecules.
Figure 4C:
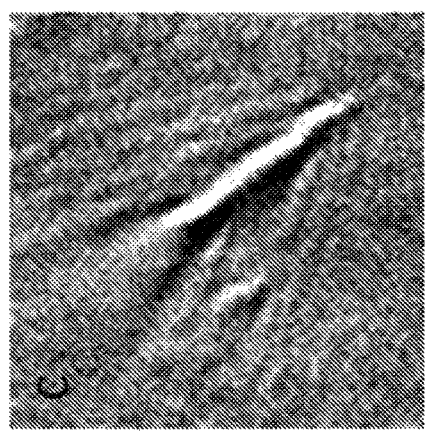

FIG. 4A shows the deconvolved image of FIG. 2B. Comparing the images after (FIG. 4B) and before (FIG. 4C) the procedure of the deconvolution, the scattering patterns were removed as intended by the algorithm. The removal of the scattering patterns allowed us to accurately measure the length of stretched DNA molecules.

Figure 4D:
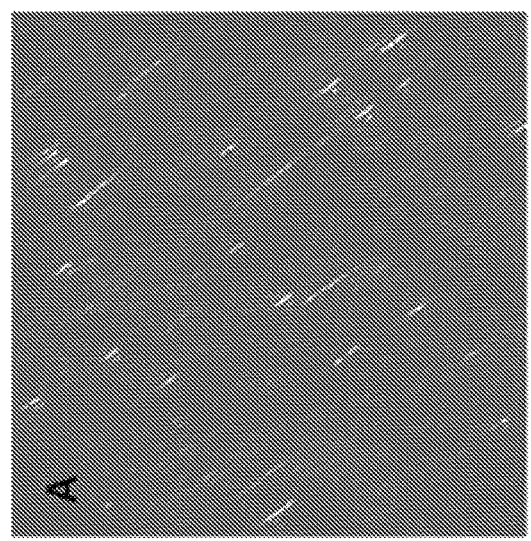
Figure 4B:
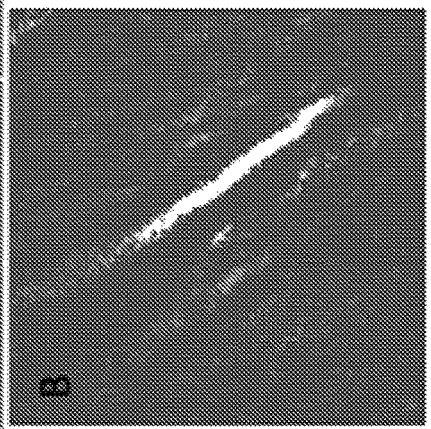

The lengths of multiple stretched DNA molecules were measured based on information available from the images and summarized in a histogram shown in FIG. 4D. By fitting the histogram to a Gaussian function, an average length of the molecule was determined to be about 14.6 μm for single stretched λ-DNA molecules, which is 15% shorter than the theoretical full-contour length of the molecules, which is explained by the DNA sample not being fully stretched. The histogram of FIG. 4D is consistent with the irradiance/intensity histogram in FIG. 2F, both showing mainly single lambda DNA stretched on surface. Compared with the fluorescent method, the DNA length measured by DSPR is free of unwanted elongation due to intercalation of dye molecules. Furthermore, since no pretreatment or modification of DNA molecule is required for DSPR imaging, the native properties of DNA are unaffected, which is important for the study of DNA with other molecules, such as proteins.

Restriction Map of DNA with DSPR Imaging.

Figure 5A:
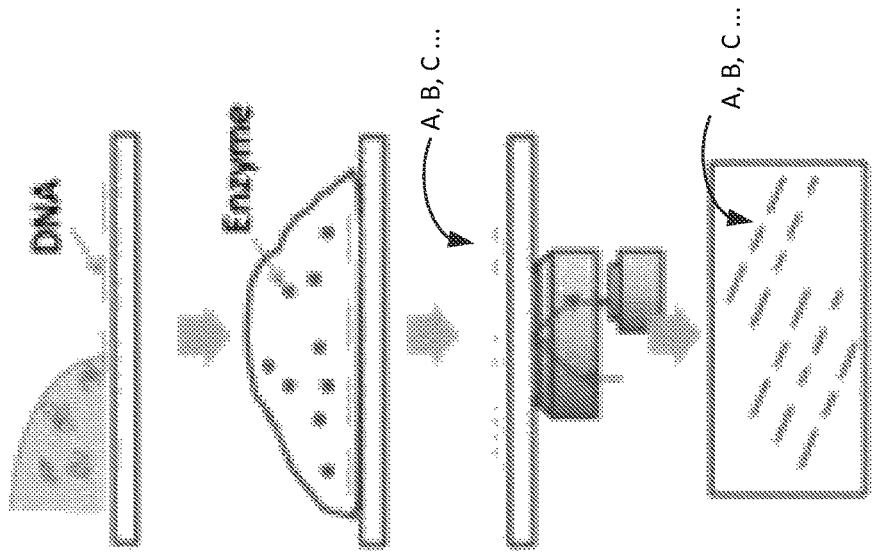
FIGS. 5A, 5B, and 5C are diagrams and graphs showing optical mapping effectuated with an embodiment of the DSPR imaging.
Figure 5B:
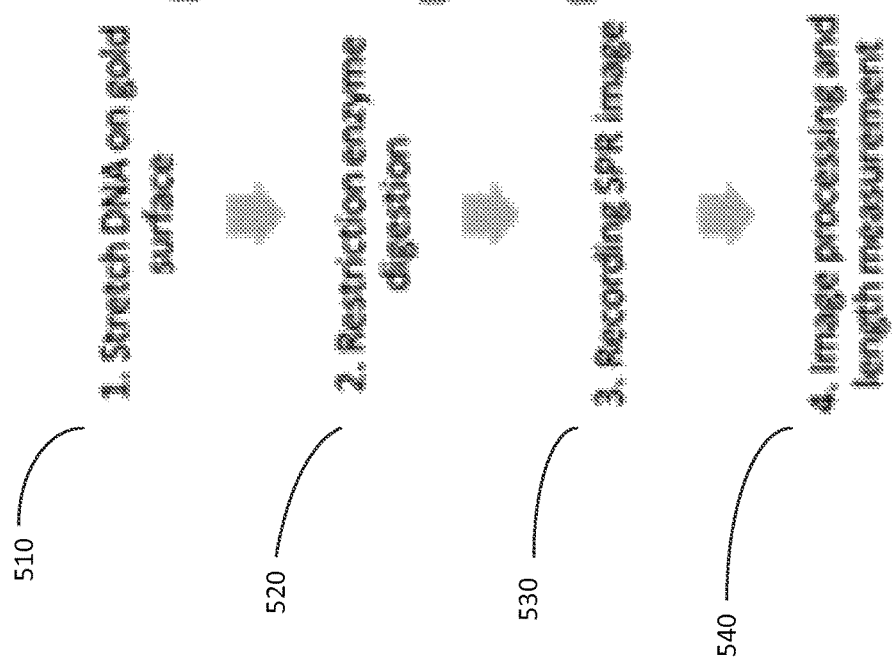

It is anticipated that the modality of label-free imaging and detection of single DNA molecules with the plasmonic technique discussed in this disclosure has many applications. What was empirically demonstrated in this investigation was the optical mapping of DNA using Sma I restriction endonucleases. In the example of FIGS. 5A, 5B, a λ-DNA molecule was stretched on gold surface after adding Sma I, at step 510. The DNA molecule was cut into small DNA fragments (A, B, C . . . ) by the enzyme, as shown at 520. These DNA fragments A, B, C . . . were then directly imaged, at step 530. with the DSPR approach without further labeling or treatments. From the images, formed at step 520, lengths of the DNA fragments were measured at step 540, and consequently, cutting sites were determined and aligned according to the length ratio among DNA fragments.

Figure 5C:
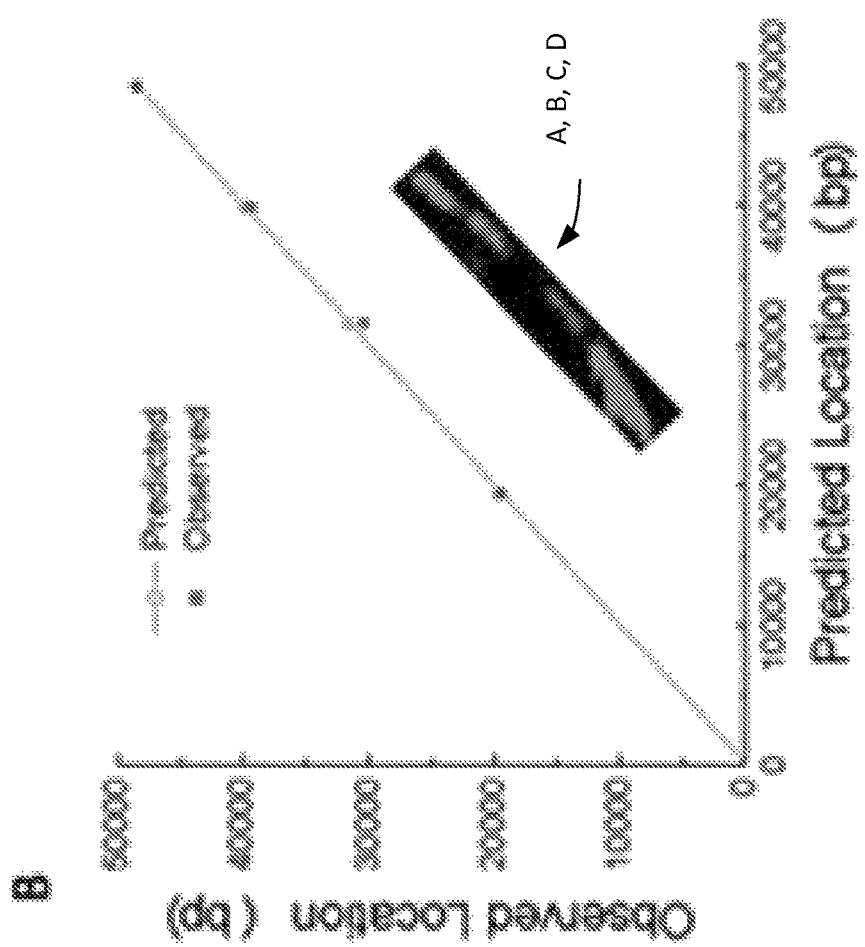
Figure 7C:
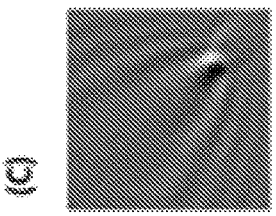
FIGS. 7A, 7B, 7C, and 7D are a set of images and graphs showing the steps of image acquisition and processing according to an embodiment of the invention. The shown DSPR images were simulated as the scattering of propagating surface plasmon (SP) wave by DNA molecules.
Figure 7B:
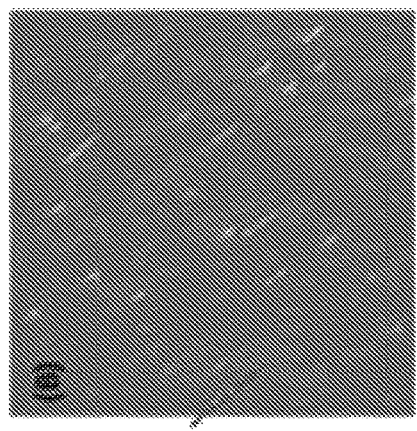
Figure 7A:
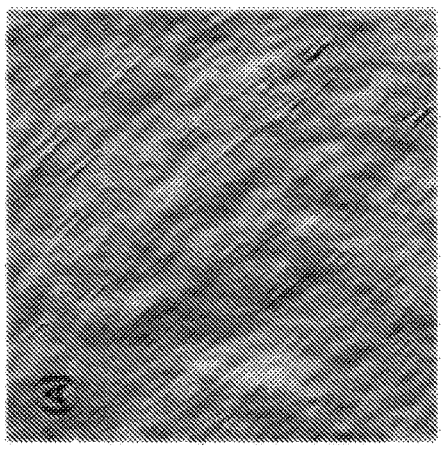
Figure 7D:
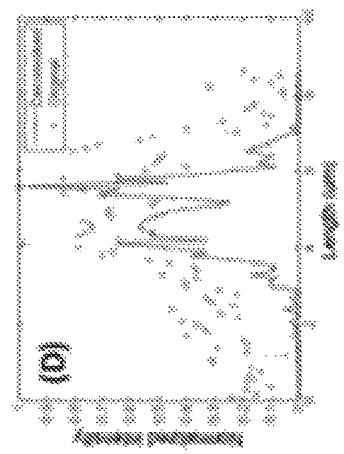

FIG. 5C shows the observed cutting sites after Sma I digestion, and the predicted cutting sites obtained from the manufacturer. Specifically, four DNA fragments (A, B, C, and D) were observed after digestion (shown in inset to FIG. 5C), and the cutting sites were determined from the fragment lengths. The DSPR imaging resolution was about 300 nm, and thus the mapping resolution was about 1 k by (assuming a 0.34 nm/bp ratio for stretched DNA molecule without fluorescent labeling). The DSPR imaging technique is fast (tome required for acquisition of an image is on the order of a millisecond or shorter) and, therefore, such imaging modality can be integrated with micro- and nano-fluidic devices, which are attractive for high throughput optical mapping of DNA. A differential plasmonic imaging technique has been disclosed developed to achieve high image contrast of optically transparent molecules. Using the technique, for the first time label-free imaging and accurate length measurement of single DNA molecules has been demonstrate. The DSPR images of DNA molecules exhibit unique scattering patterns, arising from the scattering of the surface plasmonic waves by DNA molecules. Both experiment and simulation showed that the contrast and scattering patterns of the DSPR image of DNA depend on the orientation of DNA molecule relative to the propagation direction of the plasmonic waves. The capability of label-free imaging of single DNA molecules has been used to create restriction maps of DNA. DSPR imaging of DNA molecules is label-free, fast, and quantitative, making it suitable for single molecule DNA analysis.

Figure 8:
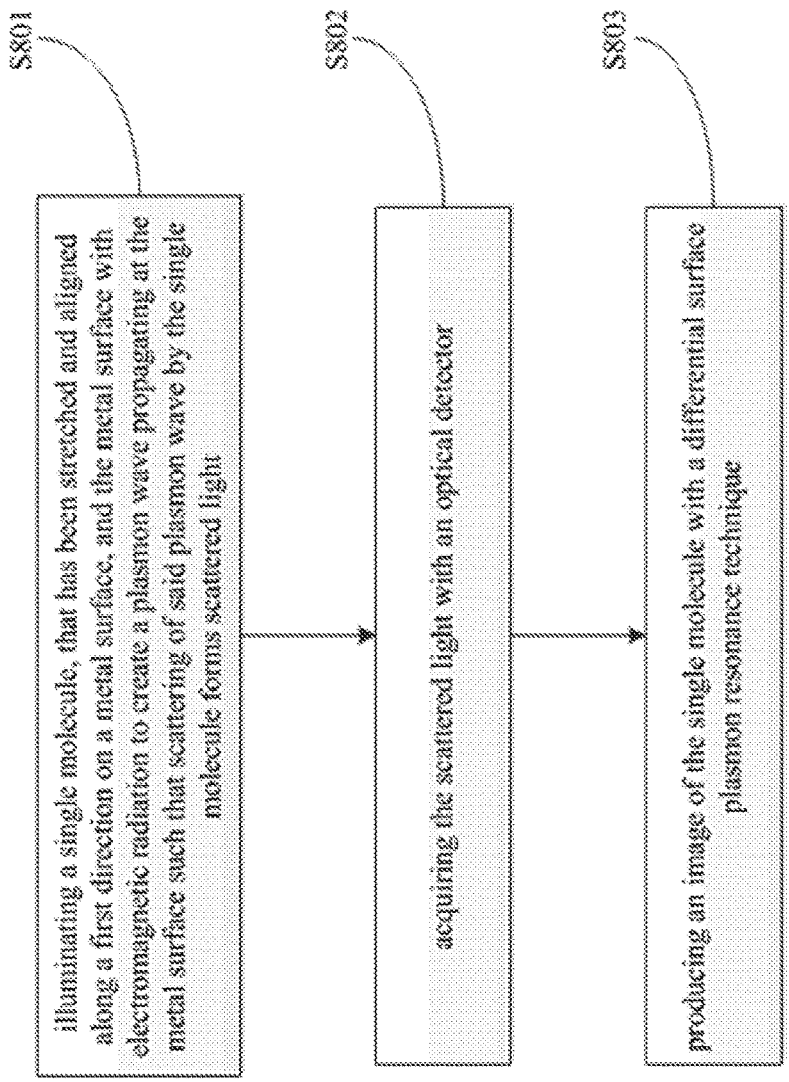
FIG. 8 is a flow-chart illustrating a method for detecting and imaging of a single molecule according to an embodiment of the present invention.

In reference to FIG. 8, an embodiment the method for detecting and imaging of a single molecule include the steps of illuminating at least one of a single molecule (that has been stretched and aligned along a first direction on a metal surface) and the metal surface with electromagnetic radiation to create a plasmon wave propagating at the metal surface such that scattering of said plasmon wave by the single molecule forms scattered light (see S801 in FIG. 8). The method further includes acquiring the scattered light with an optical detector (see S802 in FIG. 8); and producing an image of the single molecule with a differential surface plasmon resonance technique (see S803 in FIG. 8).

Therefore, label-free optical imaging of single biological molecules, DNA, was demonstrated for the first time with the use of the differential plasmonic imaging technique.

It is appreciated therefore, that embodiments of the invention provide a method for optical detection and imaging of a single molecule. Such method includes illuminating a sample attached to a substrate with light; conditioning light at the sample; recording a first image of a sample, acquired in conditioned light, with an optical detector at a first location between light-collecting optics and the substrate; and changing a location of at least one of light-collecting optics and the substrate from the first location to a second location. The method further includes forming a differential image based on the first image and optical data received by the detector after said changing. The process of changing a location may result in spatially translating the substrate between first and second positions with respect to the light-collecting optics (and, in particular, translating over a distance on the order of wavelength of light illuminating the sample). A sample may include a single molecule that has been stretched and aligned along a first direction on a metal surface of the substrate, while conditioning of light may result in scattering of light at the sample. The metal surface may include one or more of gold, silver, copper, aluminum, magnesium, platinum, palladium, cobalt, chromium, and nickel. The process of illuminating, in one implementation, results in creating a surface plasmon wave propagating along the metal surface in the first direction. A specific substrate may be configured to include a dielectric slab coated with a layer of metal, while illuminating light is chosen at such polarization, wavelength, and incident angle as to excite a surface plasmon wave propagating at the layer of the metal. The process of formation of the differential image includes subtracting optical data representing the first image from the optical data received by the detector after the change in location has occurred. IN a specific case, the formation of the differential image includes forming the differential image DI according to $$DI(x, y) = I'(x, y) - I(x, y) = \left(\frac{dI_S}{dx}\right)\Delta x,$$

wherein DI represents irradiance distribution of the differential image, $I(x,y)=I_S(x,y)+I_B(x,y)$ represents irradiance distribution of an image formed at the first spatial location, $I_S(x,y)]$ represents irradiance distribution corresponding to an SPR image of the sample, $I_B(x,y)$ represents background irradiance distribution formed by causes unrelated to interaction of light with said sample, and $I'(x,y)=I_S(x,y)+I_B(x+\Delta x, y)$ represents irradiance distribution of an image formed at the second location, the first and second locations being separated by a distance $\Delta x$. The process of changing a location may include repeatedly translating the substrate between the first location and the second location, while the formation of the differential image may include employing an algorithm to produce an optimal differential image by minimizing background noise and, in particular, based on i) calculating the differential image from images of the sample recorded at the first and second locations for each of repeated translations of the substrate, and ii) using a Fourier filter to selectively remove noise at frequencies different from a frequency at which the substrate is being translated.

Implementations of the invention also include an apparatus for detecting and imaging a sample. Such apparatus includes a substrate on which the sample is attached; a light source illuminating the sample; a unit configured to spatially translate the substrate between a first and second positions; an optical imaging system disposed to gather and analyze light from said sample to form images at the first and second positions; and electronic circuitry operably configured to produce a difference image representing a difference between said images formed at the first and second positions. (Generally, however, a difference image can be created either numerically with an imaging processing algorithm or an electronic circuitry.)

The substrate may be coated with a layer of metal and the sample may include a single molecule stretched and aligned along a first direction on a metallic surface of the layer of metal layer, while light from the light source is delivered to the substrate such that a surface plasmon wave is excited at the metallic surface. The apparatus may further include an optical system configured to collect scattered light associated with the surface plasmon wave.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

When the present disclosure describes features of the invention with reference to corresponding drawings (in which like numbers represent the same or similar elements, wherever possible), the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, at least for purposes of simplifying the given drawing and discussion, and directing the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this particular detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

The invention as recited in claims appended to this disclosure is intended to be assessed in light of the disclosure as a whole, including features disclosed in prior art to which reference is made.

Data processing, required to form images as discussed and perform image comparison, has been described as including a processor controlled by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

What is claimed is:

1. A method for label-free optical detection and imaging of a single molecule, the method comprising the steps of:
    (a) illuminating a sample attached to a substrate with light,
    (b) conditioning the light at the sample,
    (c) recording a first image of a sample, acquired in die conditioned light, with an optical detector at a first mutual orientation between light-collecting optics and the substrate;
    (d) changing a location of at least one of the light-collecting optics and the substrate from the first location to a second location; and (e) forming a differential image based on the first image and optical data received by the detector after said changing to obtain an image of said single molecule in the sample, wherein any of said illuminating, conditioning, recording, changing the location, and forming is carried out without fluorescent labelling of said single molecule.

2. A method according to claim 1, wherein said changing a location includes spatially translating the substrate between first and second positions with respect to the light-collecting optics.

3. A method according to claim 2, wherein said spatially translating includes spatially translating the substrate over a distance on the order of wavelength of light.

4. A method according to claim 1, wherein said illuminating a sample includes illuminating said molecule on a metal surface of the substrate and the metal surface with light, and wherein said conditioning includes scattering light at the sample.

5. A method according to claim 1, wherein said illuminating includes illuminating a metal surface containing one or more of gold, silver, copper, aluminum, magnesium, platinum, palladium, cobalt, chromium, and nickel, and further comprising creating a surface plasmon wave propagating along said metal surface in a first direction.

6. A method according to claim 1, wherein said illuminating includes illuminating the substrate, which comprises a dielectric slab coated with a layer of metal, with light at such polarization, wavelength, and incident angle as to excite a surface plasmon wave propagating at the layer of the metal.

7. A method according to claim 1, wherein said illuminating includes illuminating at least one of a protein, peptide, polypeptide, enzyme, protein-DNA complex, polynucleotide, antibody, DNA, RNA, siRNA, antigen, antigenic epitope, hormone, carbohydrate, lipid, phospholipid, and biotinylated probe.

8. A method according to claim 1, wherein said forming includes subtracting optical data representing the first image from said optical data received by the detector after said changing.

9. A method according to claim 1, wherein said forming includes forming the differential image according to:

$$DI(x, y) = I'(x, y) - I(x, y) = \left(\frac{dI_S}{dx}\right)\Delta x,$$

wherein $I(x, y) = I_S(x, y) + I_B(x, y)$ represents irradiance distribution of an image formed at the first spatial location, $I_S(x, y)$ represents irradiance distribution corresponding to an SPR image of the sample, $I_B(x, y)$ represents background irradiance distribution formed by causes unrelated to interaction of light with said sample, and $I'(x, y) = I_S(x, y) + I_B(x+\Delta x, y)$ represents irradiance distribution of an image formed at the second location, the first and second locations being separated by a distance $\Delta x$.

10. A method according to claim 1, wherein said changing includes repeatedly translating the substrate between the first location and the second location, and said forming includes employing an algorithm to produce an optimal differential image by minimizing background noise.

11. A method according to claim 10, wherein said employing includes calculating the difference image from images of the sample recorded at the first and second locations for each of repeated translations of the substrate, and using a Fourier filter to selectively remove noise at frequencies different from a frequency at which the substrate is being translated.

12. An apparatus for label-free detecting and imaging of a sample, the apparatus comprising a substrate on which the sample is attached; a light source illuminating the sample;

a unit configured to spatially translate the substrate between a first and second positions; an optical imaging system disposed to gather and analyze light from said sample to form images at the first and second positions; and a programmable computer processor configured to produce a differential image representing a difference between said images formed at the first and second positions to obtain an image of a single molecule in the sample, said apparatus configured to operate and produce said differential image in absence of fluorescent labelling of the sample.

13. An apparatus according to claim 12, wherein said substrate is coated with a layer of metal and said sample includes said single molecule placed on a metallic surface of said layer, wherein light from said light source is delivered to said substrate such that a surface plasmon wave is excited at the metallic surface, and further including a subsystem configured to collect scattered light associated with said surface plasmon wave.

14. An apparatus according to claim 13, wherein the metal layer includes at least one of gold, silver, copper, aluminum, magnesium, platinum, palladium, cobalt, chromium, and nickel.

15. An apparatus according to claim 12, wherein said unit includes at least one of a piezoelectric actuator and an electrical motor.

16. An apparatus according to claim 12, wherein said optical imaging system comprises a high numerical aperture oil immersion objective.

* * * * *

UNITED STATES PATENT AND TRADEMARK OFFICE
CERTIFICATE OF CORRECTION

PATENT NO. : 10,408,757 B2
APPLICATION NO. : 15/038629
DATED : September 10, 2019
INVENTOR(S) : Nongjian Tao et al.

It is certified that error appears in the above-identified patent and that said Letters Patent is hereby corrected as shown below:

In the Claims

Column 16, Line 61, (approx.), In Claim 1(c):
"recording a first image of a sample, acquired in die"
Should be:
-- recording a first image of a sample, acquired in the --

Signed and Sealed this
Twenty-ninth Day of October, 2019

Andrei Iancu
*Director of the United States Patent and Trademark Office*